United States Patent
Wegkamp et al.

(10) Patent No.: US 8,524,297 B2
(45) Date of Patent: Sep. 3, 2013

(54) **INCREASED FOLATE PRODUCTION LEVELS IN *LACTOBACILLUS* FERMENTING MELON JUICE**

(75) Inventors: Henderikus Bernardus Albertus Wegkamp, Bussum (NL); Filipe Branco dos Santos, Amsterdam (NL); Eilt Johannes Smid, Wageningen (NL); Jeroen Hugenholtz, Parleiten-Geisenfeld (DE)

(73) Assignee: Stichting Top Institute Food and Nutrition, Wageningen (NL)

( * ) Notice: Subject to any disclaimer, the term of this patent is extended or adjusted under 35 U.S.C. 154(b) by 189 days.

(21) Appl. No.: 12/811,782

(22) PCT Filed: Dec. 5, 2008

(86) PCT No.: PCT/NL2008/050769
§ 371 (c)(1),
(2), (4) Date: Feb. 23, 2011

(87) PCT Pub. No.: WO2009/072880
PCT Pub. Date: Jun. 11, 2009

(65) Prior Publication Data
US 2011/0159148 A1 Jun. 30, 2011

Related U.S. Application Data

(60) Provisional application No. 60/992,829, filed on Dec. 6, 2007.

(30) Foreign Application Priority Data

Dec. 6, 2007 (EP) .................................... 07122444

(51) Int. Cl.
*A23L 1/30* (2006.01)

(52) U.S. Cl.
USPC .......................... 426/61; 435/106; 435/252.9

(58) Field of Classification Search
USPC ................................ 426/61; 435/106, 252.9
See application file for complete search history.

(56) References Cited

FOREIGN PATENT DOCUMENTS

| | | |
|---|---|---|
| JP | 1063352 | 3/1989 |
| WO | WO2006093408 A | 9/2006 |

OTHER PUBLICATIONS

Fazeli, MR et al. 2007. Antagonistic action of watermelon juice probioticated using different strains of *Lactobacillus* against *S. typhimurium*. Iranina J. of Pub. Health. 36:70-73.*
Taranto, M. P. et al. 2003. *Lactobacillus reuteri* CRL 1098 produces cobalamin. J. Bacteriol. 185: 5643-5647.*
LeBlanc, J. G. et al. 2007. Folate production by lactic acid bacteria and other food grade microorganisms. Formatex.*
Sybesma et al.,"Effects of cultivation conditions of folate production by lactic acid bacteria," Appl Environ Microbiol. 2003, 69:4542-4548.
Edwards AJ et al., Consumptiion of Watermelon Juice Increases Plasma Concentrations of Lycopene and β-carotene in Humans. Journal of Nutrition 133:1043-50 (2003).

* cited by examiner

*Primary Examiner* — D. Lawrence Tarazano
*Assistant Examiner* — Hamid R Badr
(74) *Attorney, Agent, or Firm* — Browdy and Neimark, PLLC

(57) ABSTRACT

The invention relates to the field of food, feed and food supplements comprising high folate levels, whereby the folate is produced by fermentation of *Lactobacillus* strains on melon fruit extract. Methods for increasing folate production of *Lactobacillus* strains are also provided.

10 Claims, 2 Drawing Sheets

SEQUENCE LISTING

<160> NUMBER OF SEQ ID NOS: 4

<210> SEQ ID NO 1
<211> LENGTH: 33

```
<212> TYPE: DNA
<213> ORGANISM: Artificial Sequence
<220> FEATURE:
<223> OTHER INFORMATION: synthetic
<220> FEATURE:
<221> NAME/KEY: misc_feature
<223> OTHER INFORMATION: folBKpnF forward primer

<400> SEQUENCE: 1
gaaagaggct gggtaccatt atgggcatga ttc                                 33

<210> SEQ ID NO 2
<211> LENGTH: 26
<212> TYPE: DNA
<213> ORGANISM: Artificial Sequence
<220> FEATURE:
<223> OTHER INFORMATION: synthetic
<220> FEATURE:
<221> NAME/KEY: misc_feature
<223> OTHER INFORMATION: folPXbaR reverse primer

<400> SEQUENCE: 2
cttaacccca tctagacgta atatcg                                         26

<210> SEQ ID NO 3
<211> LENGTH: 25
<212> TYPE: DNA
<213> ORGANISM: Artificial Sequence
<220> FEATURE:
<223> OTHER INFORMATION: synthetic
<220> FEATURE:
<221> NAME/KEY: misc_feature
<223> OTHER INFORMATION: folPF forward primer

<400> SEQUENCE: 3
catggcatcg atattgaacg aattg                                          25

<210> SEQ ID NO 4
<211> LENGTH: 20
<212> TYPE: DNA
<213> ORGANISM: Artificial Sequence
<220> FEATURE:
<223> OTHER INFORMATION: synthetic
<220> FEATURE:
<221> NAME/KEY: misc_feature
<223> OTHER INFORMATION: nisRKR  reverse primer

<400> SEQUENCE: 4
gttctatcga aagcgaaatc                                                20
```

INCREASED FOLATE PRODUCTION LEVELS IN *LACTOBACILLUS* FERMENTING MELON JUICE

FIELD OF THE INVENTION

The instant invention relates to the field of microbiology and food-, feed- and food-supplement production using microbial fermentation of melon juice. Provided are methods of producing high folate levels by fermenting melon juice, as well as food-, feed- and food supplements comprising or consisting of fermented melon juice and/or folate (vitamin B9/B11) obtained from such fermentation methods. Also, the use of melon juice (or parts thereof and/or dilutions and/or concentrations thereof) as a fermentation medium or fermentation supplement of folate producing bacteria is provided herein. A further embodiment is the use of p-aminobenzoic acid or p-aminobenzoate (p-ABA) (in combination with melon juice) for increasing folate production during microbial fermentation.

General Definitions

"Lactic acid bacteria" (LAB) refers to bacteria, which produce lactic acid or another organic acid (such as propionic acid) as an end product of fermentation, such as, but not limited to, bacteria of the genus *Lactobacillus, Streptococcus, Lactococcus, Oenococcus, Leuconostoc, Pediococcus, Carnobacterium, Propionibacterium, Enterococcus* and *Bifidobacterium*.

"Food grade" are components which can safely be ingested (e.g. orally) by humans or animals.

"Probiotics" or "probiotic strain(s)" refers to strains of bacteria, which have a beneficial effect on the host when ingested by a subject and which are generally regarded as safe (GRAS) to humans.

"Food grade" refers to being regarded as safe for human and/or animal consumption, e.g. by the relevant regulatory authorities such as the US Food and Drug Administration (FDA).

"Probiotic lactic acid bacteria" are, thus, those LAB strains which also have probiotic properties, i.e. which are probiotic strains.

"Non-gmo bacterial strains" refers to strains which have not been genetically modified by human intervention, i.e. which do not comprise homologous or heterologous nucleic acid sequences introduced into the cells or genome. For example, chimeric genes (comprising operably linked nucleic acid sequences, such as a promoter, coding sequence and terminator) or vectors have not been introduced into the bacteria.

"Gmo bacterial strains" or "recombinant strains" are herein strains which have been genetically modified by human intervention, e.g. by introduction of homologous or heterologous genes into the genome, such as a chimeric gene.

"Non-mutant bacterial strains" refer herein to wild-type strains, i.e. strains which have not been treated by mutagenic agents by humans. "Wild-type" strains are strains found in, or originally isolated from, nature and which are genetically essentially the same as the wild strain.

"Melon extract" refers herein to the melon fruit extract of plants of the species *Cucumis melo*, e.g. (*C. melo* var. *reticulans*, Galia melon), Muskmelon, Cantaloupe, Hami melon, Honeydew melon (*Cucumis melo* var. *inodorus*), Piel de Sapo, and Sugar melon, *Cucumis melo* subsp. *agrestis; Cucumis melo* subsp. *melo.; Cucumis melo* var. *cantalupensis; Cucumis melo* var. *conomon*, and others.

"Melon juice" refers to the non-solid phase (liquid phase) obtained after liquidification of melon extract.

"Folate" and "folic acid" [N-[4-{[2-amino-1,4-dihydro-4-oxo-6-pteridinyl)methyl]amino}benzoyl]-L-glutamic acid] are used herein interchangeably to refer to folic acid and derivatives of folic acid, e.g. differing in oxidation state, one-carbon substitutions or the number of glutamate residues. Alternative names are vitamin B9, vitamin B10, vitamin B11, vitamin B9/B11 or vitamin M. Examples of derivatives are tetrahydrofolate, 5-formyl tetrahydrofolate, 5,10-methylene tetrahydrofolate, 10-formyl tetrahydrofolate, 5-methyl tetrahydrofolate, 5,10-methenyl tetrahydrofolate, etc. Encompassed herein are for example polyglutamyl folate and/or shorter hydrolysis products such as di-, tri- and/or monoglutamyl folate.

"p-ABA" refers to para-aminobenzoic acid or para-aminobenzoate or 4-aminobenzoic acid and is a folate building block in the folate biosynthetic pathway. GTP, p-ABA and glutamate form the precursors of folate.

"Fermentation" or "fermentation culture" refers to growth cultures used for growth of bacteria which convert carbohydrates into alcohol and/or acids, usually (but not necessarily) under anaerobic conditions.

"Fermentation medium" refers to the growth medium being used for setting up the fermentation culture, while "fermentation broth" is generally used to refer to the fermented medium (i.e. during and/or after fermentation). However, both terms may be used interchangeably herein and the meaning will be clear from the context.

"Food" or "food product" refers to liquid, semi-solid and/or solid food products (nutritional compositions), suitable for human and/or animal consumption.

"Food supplement" refers to a composition ingested by humans in addition to the normal daily food intake. Generally, food supplements are in the form of tablets, powders, sachets, pills, etc.

"Food product ingredient" or "food supplement ingredient" refers to a product which is suitable for being added to a final food product, or food supplement, or during the production process of a food product, or food supplement.

The term "comprising" is to be interpreted as specifying the presence of the stated parts, steps or components, but does not exclude the presence of one or more additional parts, steps or components.

In addition, reference to an element by the indefinite article "a" or "an" does not exclude the possibility that more than one of the element is present, unless the context clearly requires that there be one and only one of the elements. The indefinite article "a" or "an" thus usually means "at least one".

"Growth phase" refers to commonly known growth phases of microorganism, e.g. in batch fermentation cultures, such as the lag-phase, exponential growth phase and the subsequent stationary phase, followed by the death phase.

"Percentages (%) sequence identity" refers to the percentage identical nucleotides or amino acids between two sequences and can be determined using for example pairwise local alignment tools such as the program "water" of Emboss-WIN (version 2.10.0) using default parameters, (gap opening penalty 10.0 and gap extension penalty 0.5, using Blosum62 for proteins and DNAFULL matrices for nucleic acids) or "Bestfit" of GCG Wisconsin Package, available from Accelrys Inc., 9685 Scranton Road, San Diego, Calif. 92121-3752 USA, using default parameters. Alternatively, BLAST analysis using default settings may also be used, such as protein Blast of NCIMB (http://www.ncbi.nlm.nih.gov/BLAST/Blast.cgi), with a gap creation penalty 11 and gap extension penalty 1.

BACKGROUND OF THE INVENTION

Folate is essential for the human and animal diet and deficiency can result in a range of diseases and disorders, such as neural tube defects in newborns. Many plants, fungi and bacteria synthesize folate, including lactic bacteria (LAB), whereby folate concentrations in fermented dairy products are higher than in non-fermented dairy product. The annotated genome sequence of *Lactococcus lactis* subsp. *lactis* IL1403 shows the genes of the folate biosynthetic cluster. The folate genes from other gene clusters have also been identified, such as those of *Lactococcus lactis* MG1363, and are used to genetically engineer bacteria having increased folate production, for example through overexpression of the folKE gene (Sybesma et al., 2003, Applied and Environm. Microb. Vol. 69(6), pp 3069-3076). Controlled overexpression of folKE resulted in a 3-fold increase of total folate production and a 10-fold increase of extracellular folate production.

Not all LAB are able to produce folate. For example, Sybesma et al. (2003, Applied and Environm. Microbiology Vol. 69(8) pp 4542-4548) found that while *Lactococcus lactis, Streptococcus thermophilus* and *Leuconostoc* species were able to produce folate, most *Lactobacillus* species tested were not, with the exception of *L. plantarum*. Total (intracellular and extracellular) deconjugated folate levels varied widely and maximum levels were 291 µg/L for strain *L. lactis* ssp. *lactis* NZ9010 (grown aerobically on M17 culture medium; strain is defective in lactate dehydrogenase), while *L. plantarum* WCFS 1 for example only produced 45 µg/L on MRS medium. Also the proportion excreted into the medium varied.

Sybesma et al. (supra) also studied the effects of culture conditions such as pH, p-ABA and hemin on folate production and distribution in two commonly used LAB, *L. lactis* MG1363 and *S. thermophilus* NIZO strain B119. Culture media included M17 medium, Chemically Defined Medium (CDM) and MRS medium. In continuous culture an increase in pH from 5.5 to 7.5 resulted in an increased folate production in these two strains by a factor 2-3, reaching 534 µs/L for *S. thermophilus* grown on M17 medium and 107 µg/L for *L. lactis* grown on CDM. For *L. lactis*, the addition of p-ABA in concentrations ranging from 1-100 µM also increased folate production, while amounts of p-ABA above 100 µM had no effect. Interestingly, the addition of growth inhibiting substances also resulted in a folate increase.

As already mentioned, *Lactobacillus* species produce no or very low levels of folate. *Lactobacillus* species are important in the production of fermented products and an increase in folate production by those species would be highly desirable. *Lactobacillus* species are for example used industrially for the production of yogurt, cheese, sauerkraut, pickles, and other fermented foods, as well as animal feeds, such as silage. In addition, the use of natural (food grade), rather than synthetic, fermentation media has the advantage that the natural media can be used as such for food-, feed- or food supplement production, eliminating the need for purifying the folate from the culture. These objectives are met by the present invention.

WO02/097063 describes the production of bioavailable folic acid by recombinant microorganisms (genetically modified bacteria). The recombinant bacteria are grown on synthetic media.

WO2006/013588 describes folic acid producing probiotic *Bifidobacterium* strains and their use. These may be used in formulations together with other probiotic LAB.

WO2006/093408 relates to mutant bacteria which are resistant to methotrexate and overproduce folate. The bacteria are identified by using methotrexate as a selection agent. There is no indication that natural fermentation media may increase folate production.

DETAILED DESCRIPTION OF THE INVENTION

Methods of Producing Folate According to the Invention

The present invention provides methods for increasing folate levels produced by folate producing *Lactobacillus* species. The inventors found that total folate levels, and/or folate:vitamin B12 ratio, produced during fermentation of *Lactobacillus* species are significantly increased when melon extracts and/or melon juice or parts thereof or are used or added to the fermentation medium. In addition, foods such as fruit-containing or fruit derived foods are commonly preserved by fermentation, so that in accordance with the invention a method for food preservation (i.e. for reducing perishability food) is provided, whereby the resulting product has as further benefit an increased folate level and/or an increased ratio of folate to vitamin B12.

Thus in one embodiment of the invention a method for producing folate and/or for increasing total folate levels and/or for increasing the folate:vitamin B12 ratio produced by *Lactobacillus* species is provided comprising the following steps:

(a) providing an extract from a melon fruit of a *Cucumis melo* species;
(b) using all or part of the melon fruit extract to prepare a fermentation medium;
(c) inoculating said fermentation medium with one or more *Lactobacillus* strains;
(d) allowing fermentation to take place; and optionally
(e) using all or part of the fermented medium for the preparation of a food-, feed- or food supplement product with high folate levels and/or a high folate:vitamin B12 ratio.

In step (a) fruit of the species *Cucumis melo* may be used to prepare an extract. In a preferred embodiment the fruit used comprise or consist of Galia melon. An extract is prepared from parts or all of one or more fruit. Mixtures of fruit (or fruit parts) from different species, subspecies or varieties of *Cucumis melo* may be used. Preferably however no fruit of other fruit species are used for preparing the extract and/or the fermentation medium. The fruit and/or fruit pieces used may be from any fruit ripening/developmental stage of the fruit, e.g. from ripe fruit or from earlier fruit ripening/developmental stages and/or mixtures of these. Optionally fruit seeds may be removed from the fruit so that the extract is free of seeds.

The extract is preferably a liquid extract, i.e. the fruit juice. Fruit juice can be easily prepared by liquidification of fruit tissues using known methods (squashing, cutting, mashing, mixing, blending, heating, etc.) and optionally removing all or part of the solid fruit components by for example filtration or centrifugation or other methods known in the art. Preferably at least 70%, 80%, 90% or even more preferably 99% or 100% of the solid plant components are removed. The extract is preferably (but not necessarily) also sterilized, e.g. by filtration or heating, to remove or kill microorganisms (such as non-desired bacteria or fungi) present In step (b) all or part of the melon fruit extract is used to prepare a fermentation medium. In other words the fermentation medium preferably comprises or consists of melon fruit extract. Most preferably the final fermentation medium comprises at least 50% (vol/vol), more preferably at least 60%, 70%, 80%, 90% or more (e.g. 95% or 99% or 100%) melon fruit extract, e.g. melon juice, obtained directly from melon fruit. The melon fruit extract may be diluted using for example one or more food grade buffers, such as phosphate buffer, and optionally the pH is adjusted to a specific pH, such as about pH 5.0, pH 5.5, pH 6.0, pH 6.5, pH 7.0, pH 7.5 or any pH in between these values. The fermentation medium does in one embodiment not contain fruit extracts (e.g. juices) of plant species other than those derived from *Cucumis melo*.

In step (b) also several extracts of melon fruit may be mixed in the preparation of the fermentation medium. Thus, for example melon juice from one *Cucumis melo* species may be mixed with melon juice from another *Cucumis melon* species. Such mixtures have the same effect as co-extraction from different *Cucumis* melon species. In a preferred embodiment the fermentation medium comprises or consists of extract from the Galia melon.

The melon extract, such as the melon juice, need not be freshly prepared in order to make the fermentation medium, but may also be extracted and then frozen, either as extracted or as a concentrate or as a dilution (e.g. in sterile water or buffer) for later use. Likewise freeze dried melon extract and/or melon juice may be used, e.g. as such or after reconstitution with water or buffer or the like.

All components used in the preparation of the fermentation medium are preferably food grade. Apart from melon fruit extract(s) the fermentation medium may also comprise buffering agents, dilution agents (water, buffer), additional amino acids (e.g. folate building blocks, such as methionine, serine, glycine, thymine, inosine, xanthine, adenine and/or guanine), sugars, flavorings, coloring agents, nucleobases, nucleosides, additional carbon sources, etc. The use of additives depend also on the further use of the fermented medium (or parts thereof) and whether the fermented medium is to be used as an additive to make a folate fortified food or feed or whether it is used as such, e.g. in capsule or powder form (as a food or feed supplement) or whether the produced folate is to be purified from the fermented medium or used together with all or part of the medium.

In one embodiment of the invention p-ABA is added to the fermentation medium in an amount which enhances folate yield compared to fermentation in the absence of additional p-ABA. Preferably at least 5 mg p-ABA are added per liter fermentation medium and/or per liter melon juice and/or melon extract, more preferably at least 10 mg, 20 mg, 30 mg, 40 mg, 50 mg, 60 mg, 70 mg, 80 mg, 90 mg or 100 mg per liter. Also more p-ABA may be added, such as at least about 150 mg, 200 mg, 500 mg, 1000 mg per Liter fermentation medium, or more. p-ABA can be obtained commercially in different purity grades from Sigma Aldrich Inc. (St. Louis, Mo., USA, see e.g. catalogue number A9878). Although not all *Lactobacillus* strains respond to p-ABA by producing more folate, the skilled person can easily determine whether p-ABA addition has a folate enhancing effect for a given strain. *Lactobacillus plantarum* strains, for example strain WCFS1, do respond positively to p-ABA addition.

It is also an embodiment of the invention that the folate producing bacterial strain itself produces p-ABA, e.g. naturally or after genetic modification (see e.g. Wegkamp et al. 2007, Applied and Environmental Microbiology Vol. 73, p 2673-2681), and/or that one or more additional strains which produce p-ABA (naturally or after modification) are added to the medium. The p-ABA gene cluster from other bacteria, such as the p-ABA biosynthetic gene cluster of *Lactococcus lactis*, can thus be introduced and overexpressed in the folate producing strain and/or in another strain, which can then be co-inoculated in step (c).

In step (c) a suitable amount of one or more *Lactobacillus* strains is used as inoculums of the fermentation medium. Inoculum amounts may vary, but in general a culture having a concentration of about $1\times10^5$-$1\times10^{10}$ cells/ml (e.g. about $1\times10^8$/ml) live or viable bacterial cells may be added to the fermentation medium at about 1% volume of the final volume of the fermentation medium, or more, or less (e.g. 0.8%, 0.5% volume).

In principle any *Lactobacillus* strain which is capable of producing folate at all (i.e. which comprises the folate biosynthetic genes) can be used, including natural/wild type strains, recombinant (gmo) strains and mutant strains. Recombinant strains may also be strains which have been transformed with one or more folate biosynthetic genes, as also folate production levels of these strains can be increased further when using the methods according to the invention. For example, the folate biosynthetic gene cluster can be cloned and/or introduced from one strain into another strain. Vector pNZ7026 carries the folate gene cluster of *L. plantarum* WCFS1 (see Examples) and this gene cluster can, thus, be introduced into other *Lactobacillus* strains by e.g. electroporation or conjugation or the genes (folB, folK, folE, folC2, xtp2, folP) can be used to identify and isolate homologous genes from other *Lactobacillus* species or strains.

One can easily test whether a strain is capable of producing folate at all, by e.g. culturing the strain on an appropriate medium and analyzing and/or quantifying whether folate is produced intracellularly and/or extracellularly using e.g. HPLC, LC-MS, microbiological assay and the like. Inoculation of the fermentation medium is done using standard microbiological methods, such as e.g. preparing fresh starter cultures of the strains(s) and/or using previously prepared inoculum such as frozen bacterial stocks having a defined amount of bacterial cells. Strains which contain the folate biosynthetic gene cluster or orthologs thereof (e.g. sequences comprising at least 40%, 50%, 60%, 70%, 80%, 90%, 95%, 98%, or more sequence identity on nucleic acid and/or amino acid level to the folate biosynthetic genes and/or proteins), for example to those of *L. plantarum* WCFS1, are likely to be able to produce folate. Thus, genetic and/or bioinformatics analysis can also be used to identify appropriate strains.

In a preferred embodiment natural/wild type (non-gmo and non-mutant) strains are used, i.e. strains as isolated from natural sources or non-modified derivatives thereof. Such strains are available at strain depository institutions or can be isolated from natural sources. The strain(s) used are preferably all be food grade, i.e. they should have (or should be able to obtain) GRAS status. Also, the strains are preferably probiotic strains. Examples of strains include *Lactobacillus* strains belonging to the following species: *L. reuteri, L. plantarum, L. rhamnosus, L. casei, L. paracasei, L. helveticus, L. delbrueckii, L. brevis, L. crispatus, L. sakei, L. jensenii, L. sanfransiscensis, L. fructivorans, L. kefiri, L. curvatus, L. paraplantarum, L. kefirgranum, L. parakefir, L. fermentum, L. acidophilus, L. johnsonii, L. gasseri, L. xylosus, L. salivarius, L. murinus, L. minutis, L. gallinarium, L. amylovorus*, etc.

Useful strains are for example (but not limited hereto) the following strains: *L. plantarum* WCFS1, *L. reuteri* 100-23, *L. reuteri* JCM1112, *L. delbrueckii* subsp. *bulgaricus* ATCCBAA 365, *L. delbrueckii* subsp. *bulgaricus* ATCC 11842, and *L. sake* subsp. *sakei* 23 K (species known to possess the folate gene cluster, according to the ERGO™ bioinformatics database, see Overbeek et al., Nucleic Acids Res. 2003 Jan. 1; vol 31(1):164-71).

Thus, in one embodiment one or more (preferably) food-grade and/or probiotic LAB strains (of the genus *Lactobacillus*) and/or species are use in the method.

For certain applications, such as for the preparation of foods or food supplements for e.g. vegetarians, it is also desired that the strain not only produces folate during fermentation but also vitamin B12. Thus in one embodiment of the invention the *Lactobacillus* strain used is capable of producing both folate and vitamin B12. Preferably the strain(s) is/are probiotic strains. An example of a *Lactobacillus* species which is capable hereof is *Lactobacillus* reuteri, e.g. *L. reuteri* JCM1112, but more species and/or strains may be found, for example in the genera *Clostridium, Geobacillus, Listeria, Propionibacterium, Fusobacterium, Salmonella*, amongst others. Strict vegetarian diets are often low in vitamin B12, while they are relatively rich in folate. This leads to the risk that vitamin B12 deficiency is masked by folate, whereby a need for products comprising both folate and vitamin B12 exists.

The Examples show that folate production by *L. plantarum* strain WCFS1 (originally obtained from human saliva; Accession number NCIMB 8826, National Collection of Industrial and Marine Bacteria, Aberdeen, U.K) was increased 2-3 fold on melon juice medium (about 58 µg/L medium) compared to synthetic medium (CDM) (29 µg/L medium). Folate production of strain *L. reuteri* JCM112 (originally obtained from human intestine; Accession number NCIMB 11951, National Collection of Industrial and Marine Bacteria, Aberdeen, U.K) increased almost 10 fold, from 8-35 µg/L on CDM to 310 µg/L on melon juice medium. The use of these two strains for folate production and optionally also concomitant vitamin B12 production (by e.g. *L. reuteri*) according to the invention is also an embodiment herein. These two strains may also be used as controls in the described method.

When using at least one strain capable of producing both folate and vitamin B12, the ratio of folate:vitamin B12 in the fermentation broth is increased significantly during and/or at the end of fermentation (i.e. during the stationary phase), resulting in a deviation from the common 1:1 ratio of folate:vitamin B12. The resulting folate:vitamin B12 ratio is preferably at least 2:1, 5:1, 10:1, 50:1, 100:1, 150:1, 200:1, 250:1, or more, or any ratio in between these. See e.g. Example 3 and FIG. 2, showing that wild type and recombinant folate overexpressing strains produce a significantly increased folate:vitamin B12 ratio on melon medium according to the invention compared to other media, such as CDM or cucumber medium.

Optionally, one may alternatively or in addition use different strains during the fermentation process (i.e. mixtures of strains), whereby at least one strain produces increased folate amounts and at least one other strain produces vitamin B12. For example archaea do not produce folate, but do produce vitamin B12. Thus a co-inoculation of a folate producing strain with a suitable amount a vitamin B12 producing strain is also an embodiment herein. The skilled person can easily identify bacterial strains or other micro-organisms such as archaea, yeasts or fungi, which produce vitamin B12.

Vitamin B12 can be measure and/or quantified in the fermentation broth using standard methods, such as those mentioned for folate quantification.

The folate yield obtained from fermentation on melon extract medium is significantly higher than compared to folate yield from fermentation using the same strain on CDM (chemically defined medium, as described in Teusink, B., van Enckevort, F. H., Francke, C., Wiersma, A., Wegkamp, A., Smid, E. J. and Siezen, R. J., 2005, *Appl Environ Microbiol* 71, 7253-7262). "Significantly higher" refers to at least 2×, preferably at least about 3×, 4×, 5×, 6×, 7×, 8×, 9×, 10×, 15×, 16×, or more, total folate (the sum of intracellular and extracellular folate, corrected for background folate being present in the medium) being produced by the end of fermentation (in the fermentation broth) compared to fermentation on CDM. Background folate levels are preferably determined in medium not inoculated with bacteria but which is otherwise treated the same way. For example, fermentation broth comprising (during and/or after fermentation according to the invention) a total amount of folate of at least about 40, 50, 60, 70, 80, 90, 100, 150, 200, 250, 300, 350, 400, 450, 500, 550, 600, 650, 700, 750, 800, 850, 900, 1000 µg or more folate per Liter fermentation broth is provided herein, depending on the strain or combination of strains used. Even higher levels can be achieved, for example if one or more gmo strains (e.g. folate overproducing) are used, and optionally also p-ABA is added, folate can be produced according to the instant invention in amounts of at least 2000, 3000, 4000, 5000, 6000, 7000, 8000 µg folate or more per liter fermentation broth (see Examples).

Total folate content can be measure using known techniques, such as for example the microbiological assay described by Horne and Patterson (1988, Clin Chem 34:2357-2359) or by Sybesma et al. 2003 (Appl. Environm. Microbiol 69: 3069-3076). Other quantitative assays include for example HPLC or LC-MS analysis. Folate is preferably measured at the end of fermentation, i.e. during stationary phase of the inoculum strains.

Suitable amounts of inoculum of each *Lactobacillus* strain may vary, but generally about 1% volume of a full-grown culture (containing e.g. about $1*10^8$ cells per ml) is added to fresh fermentation medium. To produce inoculum standard microbiological methods may be used.

When using mixtures of 2 or more *Lactobacillus* strains inoculum levels may be adapted, however, total volume of inoculum (of 2 or more strains) does preferably not exceed 1% of the volume of the final fermentation medium.

Optionally other food grade folate producing bacteria and/or other food grade bacteria, such as probiotic strains may be added to the fermentation medium prior and/or during fermentation and/or after fermentation and/or to the food-, feed- or nutraceutical product made and comprising (or consisting of) melon extract fermented medium (see further below). However, in one embodiment preferably the fermentation medium is not inoculated with any other microorganisms other than the selected folate (and/or vitamin B12) producing *Lactobacillus* strain(s), and optionally one or more vitamin B12 producing microorganism(s). The medium is, thus, in one embodiment free of non-food grade microorganisms, pathogenic microorganisms, spoilage microorganisms and/or any other, non-desired and/or non-inoculated bacterial species or strain, such as e.g. *Bifidobacterium, Enterococcus, Streptococcus*, and/or *Lactococcus* strains, or others.

The fermentation according to step (d) is carried out using standard methods, as e.g. described in the Examples.

After fermentation has taken place for a suitable period, preferably until no further increase in optical density is observed, the fermented medium (also referred herein as the "fermentation broth") (or a part thereof) is optionally used further to e.g. purify folate there from and/or to make products comprising or consisting of the fermented medium (or parts thereof) comprising the folate produced by the *Lactobacillus* strain(s).

Also parts of the fermented medium may be used. For example the bacteria may be removed from the medium (e.g. by filtration or centrifugation) and the bacteria-free medium may be used further. Alternatively, the fermented medium comprising the bacteria may be used as such. This is particularly attractive in cases wherein the LAB used is a probiotic strain, especially a probiotic LAB strain capable of producing both folate and vitamin B12 by itself. A further option is to kill or inactivate most of or all of the bacteria, e.g. by heating or sonication.

When making a food or feed product or nutraceutical product comprising or consisting of fermentation medium made according to the invention (or a part thereof), it is an embodiment to add the fermentation broth (or part thereof), comprising the live and/or viable bacteria, to the product or product ingredients, e.g. to add it at the beginning, during and/or after the food or feed production process.

Products and Compositions According to the Invention

Also provided are compositions and products comprising or consisting of fermentation broth (or one or more parts thereof) prepared according to the above method.

The fermented medium (the fermentation broth) is in one embodiment used as such, but may optionally be concentrated or diluted or pre-treated prior to being used to prepare a food-, feed- or food supplement composition. Pre-treatments include filtration and/or centrifugation, sterilization, freeze-drying, freezing, and the like. The fermentation medium as such and/or the pre-treated fermentation medium are in essence the primary products of the above method. These primary products may be used as such or may be used as a food product- and/or food supplement ingredient, i.e. a suitable amount of primary product may be used as ingredient when making a final food- or food-supplement product.

For example fermentation broth and/or the pre-treated fermentation broth may be used as ingredients in the preparation of folate fortified food, feed or food supplement products such as liquid foods (e.g. drinks, soups, yoghurts or yoghurt based drinks, milk shakes, soft drinks, fruit drinks, fermented dairy product, meal replacers, fermented fruit and/or juice products, etc.) or solid foods/feeds (meals, meal replacers, snacks such as candy bars, animal feed, fermented dairy products, fermented food or feed products, ice products, freeze dried food additives, cheeses, etc.) or semi-solid foods (deserts, etc.). The fermented medium and/or the pre-treated fermentation medium may simply be added to, or used during the production process of such products.

The fermentation broth obtained from the above fermentation method may be pre-treated by concentration, dilution, filtration and/or lyophilization (freeze-drying) prior to being used as product or product ingredient. Concentration and dilution with water or buffer or other food grade liquids (e.g. fruit juices, milk, etc.) can be carried out to arrive at an appropriate folate level in the final food, feed or food-supplement product. Filtration may be used to remove bacteria from the broth. In one embodiment of the invention the fermentation broth (or a concentrate, dilution and/or filtrate thereof) is freeze dried to make a folate-fortified powder. Such powder is then used in the preparation of a food, feed or food supplement in solid, liquid or semi-solid form. Supplements may be formulated as drinks, tablets, capsules, gels, powders, pills, etc. whereby the supplement comprises a suitable amount of primary product and thereby also a suitable amount of folate.

Although the fermentation broth may be pre-treated to remove and/or inactivate the bacteria, it is preferred in certain embodiments of the invention that the bacteria are not removed and/or are not inactivated, especially if the bacteria have probiotic properties. Thus, preferably the compositions according to the invention comprise live and/or viable (e.g. freeze-dried) bacteria.

The food, feed or food supplement compositions according to the invention comprise or consist of a suitable amount of primary product (fermentation broth, e.g. as such or pre-treated). The amount of primary product to be used in the preparation of the composition will vary, depending on the concentration of folate in the fermentation broth and on the amount desired to be present in the composition to be made. Preferably the product comprises an amount of folate which is equivalent to at least about 20%, 25%, 30%, 40%, 50%, 60%, 70%, 80%, 90%, more preferably 100%, 150%, 200%, 300% or more of the recommended daily amount of folate. A composition for pregnant women or those who want to become pregnant may, for example, comprise an amount of fermentation broth which provides e.g. about 400 µg folate per day or 600 µg folate per day (200% or 300% Recommended Daily Allowance), while compositions for non-pregnant subjects may comprise about 200 µg folate/day (100% Recommended Daily Allowance). It is noted that recommended intake levels varies between countries, ranging from 200 to 400 µg folate per day for none-pregnant and pregnant individuals, respectively, in Europe, whereas these levels are higher in the USA, where 400 and 600 µg folate are recommended for none-pregnant and pregnant individuals, respectively. Thus, the composition may for example comprise between about 20 µg and 600 µg folate per daily dosage, or more. As mentioned the RDA for different countries may be different, so that effectively different amounts of folate may be present in the products made for different markets.

In one embodiment the composition further comprises vitamin B12, preferably in the RDA for vitamin B12. Preferably the vitamin B12 and the folate are produced by the same microorganism (i.e. by a single strain, e.g. *L. reuteri*) in the method according to the invention, or at least they are produced in the same fermentation process (i.e. by the same or by different strains added to the fermentation medium).

When preparing a food-, feed- or food supplement comprising or consisting of primary ingredients obtainable according to the above method, obviously standard food/feed/food-supplement production and formulation methods may be followed. For example, other components may be added during the production process, such as proteins, carbohydrates, fats, minerals (iron, calcium, copper, magnesium, selenium, zinc, etc.), prebiotics, other vitamins (vitamin B1, B2, B3, B5, B6, B12, C, D, E, beta-carotene, biotin, etc.), binding agents, wetting agents, coloring agents, flavouring agents, stabilizers, emulsifiers, etc. If vitamin B12 is already present in a desired amount in the fermentation broth (e.g. RDA is about 1 µg for humans), further addition may not be desired. In addition, other bioactive ingredients may be added and may be comprised in the final product, such as probiotic bacteria, drugs, etc.

Daily amounts of folate and/or vitamin B12 may of course be either administered at once or may be subdivided into two, three or more dosages per day. The compositions may, thus, also comprise or consist of fermentation broth suitable for a single administration per day or for several daily administrations.

For some subjects daily intake is not necessary and products which provide folate may be consumed only once every few days or once a week, or less frequently. For example folate fortified food or feed products (e.g. the fermented food or feed products) need not be taken daily, although it appears to be better to take too much folate than too little, as deficiency is more dramatic than overdosing. A daily intake (one or more times per day) is thus a preferred embodiment herein.

The products according to the invention are preferably for oral intake by humans and/or animals, such as companion animals (dogs, cats, etc.) or farm animals (cows, horses, pigs, chickens, sheep, etc.) or any other animal (wild animals, e.g. kept in zoos, etc.). The products are especially suitable for subjects in need of a more regulated folate intake or subjects in need of an enhanced folate intake, such as athletes, pregnant women, folate deficient subjects, and the like.

Preferred products include for example melon juice based drinks, or melon squash based drinks, containing high folate and preferably also vitamin B12 levels and which preferably have a long shelf-life for transport and storage, especially in less developed countries where people suffering from vitamin deficiencies can targeted (therapeutically or prophylactically).

Fermentation Medium and Fermentation Broth According to the Invention

The fermentation medium and/or fermentation broth is also an embodiment herein as such. Thus in one embodiment a *Lactobacillus* fermentation medium is provided which comprises or consists of melon fruit extract as described above. In a further embodiment a fermentation broth (as such and/or pre-treated) is provided, as described, which can be used to make folate fortified food, feed or food supplements. This primary product may also be stored for longer periods e.g. frozen or freeze dried before it is used as ingredient for production of the final product.

Uses According to the Invention

In a further embodiment the use of melon fruit extract for the preparation of fermentation medium (as described above) is provided.

In addition the use of the fermentation broth, obtainable from *Lactobacillus* fermentation of the fermentation medium (comprising or consisting of melon fruit extract), for the preparation of a food-, feed- or food-supplement product is provided herein.

The following non-limiting examples illustrate the invention. Unless stated otherwise, the practice of the invention will employ standard conventional methods of molecular biology, pharmacology, microbiology or biochemistry. Such techniques are described in Sambrook and Russell (2001) Molecular Cloning: A Laboratory Manual, Third Edition, Cold Spring Harbor Laboratory Press, NY, in Volumes 1 and 2 of Ausubel et al. (1994) Current Protocols in Molecular Biology, Current Protocols, USA and Remington's Pharmaceutical Sciences, Mack Publishing Company, Philadelphia, Pa., 17th ed. (1985), Microbiology: A Laboratory Manual (6th Edition) by James Cappuccino, Laboratory Methods in Food Microbiology (3rd edition) by W. Harrigan (Author) Academic Press, all incorporated herein by reference.

EXAMPLES

1. Fermentation on 80% Melon Juice Compared to Fermentation on CDM

In this example it was determined whether melon juice fermentation yielded higher folate production pools when compared to CDM 1.1 Material and Methods 1.1.1 Strains and Inoculum Preparation The following strains were used:

*Lactobacillus reuteri* JCM1112 and *Lactobacillus plantarum* WCFS1. For both strains a 1% inoculum was used for inoculation of the developed media. The human isolate *L. reuteri* JCM1112$^T$ was obtained from the Japanese Collection of Microorganisms (RIKEN BioResource Center, 2-1 Hirosawa, Wako, Saitama 351-0198, Japan). *L. plantarum* WCFS1, a human isolate obtained from the NIZO food research culture collection (Ede, The Netherlands).

1.1.2 Construction of the Folate Overproducing Strains

The genomic DNA of *L. plantarum* WCFS 1 was isolated using established procedures (Ferain, T., Garmyn, D., Bernard, N., Hols, P. and Delcour, J. (1994) *Lactobacillus plantarum* ldhL gene: overexpression and deletion. *J Bacteriol* 176, 596-601). PCR was performed as follows; 30 sec. denaturation at 94° C., 30 sec. primer annealing at 45° C., and elongation at 68° C. for 1 min per kilo-base, this specific sequence was repeated for 30 cycles. Pfx polymerase (Invitrogen, Breda, The Netherlands) was used for amplification. DNA ligation was performed using T4 DNA ligase (Invitrogen) by overnight incubation at 16° C., DNA fragments were mixed with a 1:5 ratio of plasmid:insert: The folate gene cluster was amplified by PCR using folBKpnF (forward primer, GAAAGAGGCTGGGTACCATTATGGGCAT GATTC) (SEQ ID NO:1), and folPXbaR (reverse primer CTTAACCCCATCTAGACGTAATATCG) (SEQ ID NO:2). The folBKpnF and folPXbaR primers were modified in their sequence to introduce a KpnI, and XbaI restriction site, respectively (modified bases underlined). The folate gene cluster was amplified from 18 basepairs upstream of folB to 52 bases downstream of folP. The linear stretch of amplified DNA was partially digested, by KpnI (Invitrogen) and XbaI (Invitrogen). Partial digestion is essential because folP contains an additional XbaI restriction site. The digested folate gene-cluster, contains the full length of the folate gene cluster. Plasmid pNZ7021 (Wegkamp, A., van Oorschot, W., de Vos, W. M. and Smid, E. J. (2007) Characterization of the Role of para-Aminobenzoic Acid Biosynthesis in Folate Production by *Lactococcus lactis. Appl Environ Microbiol* 73, 2673-2681) was also digested with XbaI and KpnI. Both digested pieces of DNA were mixed in a 1:5 ratio (plasmid:insert), and were ligated by T4 DNA ligase. The ligated DNA was transferred to competent cells of NZ9000ΔylG *L. lactis* (Klaus et al. 2005) strains using electroporation by established procedures (de Vos, W. M., Vos, P., de Haard, H. and Boerrigter, I. (1989) Cloning and expression of the *Lactococcus lactis* subsp. *cremoris* SK11 gene encoding an extracellular serine proteinase. Gene 85, 169-176). Subsequently, the transformed *L. lactis* strain was cultivated for 40 hours on M17 plates with 10 mg/L CM. Chloramphenicol resistant colonies were checked for the presence of the plasmid by PCR using folPF (forward primer, CATGGCATCGATATTGAAC-GAATTG) (SEQ ID NO:3); and nisRKR (reverse primer, GTTCTATCGAAAGCGAAATC) (SEQ ID NO:4). Positive transformants were picked and inoculated on M17 broth with 10 mg/L CM. Total plasmid content was isolated from full grown overnight cultures and plasmids were isolated using Jetstar columns (Genomed GmbH, Bad Oeynhausen, Germany). The plasmid was checked by restriction analysis and subsequently sequenced using standard procedures as described below. The resulting plasmid was designated as pNZ7026. Next, plasmids pNZ7021 and pNZ7026 were transferred to competent cells of *L. reuteri* by electroporation as described elsewhere (Walter, J. N. C. Heng, W. P. Hammes, D. M. Loach, G. W. Tannock, and C. Hertel. 2003. Identification of *Lactobacillus reuteri* genes specifically induced in the mouse gastrointestinal tract. Appl Environ Microbiol 69:2044-51). Transformants were grown for 40 hours on MRS plates with 10 mg/L CM and CM resistant cells were analyzed for the presence of the appropriate plasmids by PCR. For *L. plantarum* containing the pNZ7026, primers folpF and nisRKR were used as probes. The primers CmdownF (forward primer) and nisRKR were used for monitoring the presence of pNZ7021 in the host strain.

1.1.3 Preparation of Fermentation Medium and CDM

Chemically Defined Media was made as described by Teusink, B., van Enckevort, F. H., Francke, C., Wiersma, A., Wegkamp, A., Smid, E. J. and Siezen, R. J., 2005, *Appl Environ Microbiol* 71, 7253-7262). Melon juice was made as described below. Melon media was made from *Cucumis melo* var. *reticulates* after peeling and removal of seeds. The melon was liquidified using a kitchen blender and the resulting paste was squeezed through a cotton cloth. The flow through was centrifuged twice at 10.000 RPM for 10 min at room temperature using a Sorvall centrifuge (Newton, Conn., USA). The supernatant was stored at −20° C. until further use. Before inoculation, the melon media was diluted with a 0.5 M potassium-phosphate buffer (pH 5.8) in a 4:1 ratio (v/v). The final pH was adjusted to 6.0 and the melon media medium was forced through a 0.22 μm filter to assure sterility. When mentioned, both fruit media were supplemented with p-ABA till a final concentration of 10 mg/L.

1.1.4 Fermentation

The melon and cucumber media were inoculation with *L. reuteri* wild-type, control (pNZ7021; empty vector) and folate overproducer (pNZ7026; folate gene cluster overexpressing plasmid). For *L. plantarum* WCFS1 the wild-type was inoculated. Inoculated media were cultivated for 40 hours at 37° C.

1.1.5 Folate Measurements

Total folate content was measured using the microbiological assay described by Horne and Patterson (1988, Clin Chem 34:2357-2359) or by Sybesma et al. 2003 (Appl. Environm. Microbiol 69: 3069-3076). Folate samples were taken after approximately 40 hours of growth from culture from stationary phase. Additionally, the background levels of these vitamins were determined from samples treated identically but not inoculated.

1.2 Results

The folate production levels were determined for *L. reuteri* and *L. plantarum* on CDM and 80% melon juice.

Results are shown in Tables 1 and 2 for *L. reuteri* JCM1112 and in Tables 3 and 4 for *L. plantarum* WCFS1.

TABLE 1

Fermentation of *L. reuteri* strain JCM1112 on 80% melon juice medium

| Strain | Total folate production pool μg/L | Standard deviation, μg/L | Total folate production pool μg/L per OD$_{600}$ | Fold* increase of folate pools compared to Table 2 |
|---|---|---|---|---|
| Wild type JCM1112 | 325.12 | 12.96 | 103.65 | 5.4× |
| +pNZ7021[a] | 321.34 | 5.51 | 131.66 | 4.6× |
| +pNZ7026[b] | 237.01 | 14.61 | 115.96 | n.d. |
| +pNZ7026 + p-ABA[c] | 7451.09 | 182.11 | 2518.17 | 1.67× |
| Blanc[d] | 22 | 1 | | | n.d. = not determined
[a]empty vector
[b]folate overproduction plasmid
[b]folate overproduction plasmid, containing additional 10 mg/L p-ABA
[d]melon juice
*fold increase is calculated based on the total folate production pool.

TABLE 2

Fermentation of *L. reuteri* strain JCM1112 on CDM medium with p-ABA

| Strain | Total folate production pool μg/L | Standard deviation, μg/L | OD$_{600}$ |
|---|---|---|---|
| Wild type JCM1112 | 59.92 | 5 | 2.84 |
| +pNZ7021[a] | 69.05 | 8 | 2.75 |
| +pNZ7026[b] | 4449.05 | 201 | 2.42 |

[a]empty vector
[b]folate overproduction plasmid

TABLE 3

Fermentation of *L. plantarum* WCFS1 on 80% melon juice medium

| Strain | Total folate production pool μg/L | Standard deviation, μg/L | Total folate production pool μg/L per OD$_{600}$ | Fold* increase of folate pools compared to Table 4 |
|---|---|---|---|---|
| Wild type WCFS1 | 394.51 | 1.00 | 96.63 | 13.6× |
| Blanc[a] | 22 | 1 | | |

[a]melon juice
*fold increase is calculated based on the total folate production pool.

TABLE 4

Fermentation of *L. plantarum* strain WCFS1 on CDM medium with p-ABA

| Strain | Total folate production pool μg/L | Standard deviation, μg/L | OD$_{600}$ |
|---|---|---|---|
| Wild type WCFS1 | 29 | 3 | 3.53 |

1.3 Conclusion

The results show that folate production of both wild-type and recombinant *Lactobacillus* strains can be significantly enhanced when melon juice is used as fermentation medium, when compared to CDM.

Example 2

In this Example the possibility of extending the findings described above for other fruit representatives of the genus *Cucumis* was investigated. The same experiment was tested using cucumber juice, *Cucumis sativus*.

2.1.1 Strains and Inoculum Preparation

The following strains were used: *Lactobacillus* reuteri JCM1112. A 1% inoculum was used for inoculation of the developed media.

2.1.2 Preparation of Fermentation Medium and CDM

Chemically Defined Media was made as described by Teusink, B., van Enckevort, F. H., Francke, C., Wiersma, A., Wegkamp, A., Smid, E. J. and Siezen, R. J., 2005, *Appl Environ Microbiol* 71, 7253-7262). Cucumber juice was made as follows. Cucumber juice media was prepared by liquidification of intact cucumber (*Cucumis sativus*) using a kitchen blender (Moulinex, Masterchef 370, France). The resulting paste was forced through a cotton cloth, and the flowthrough was filtrated with a cellulose filter (0.15 mm) before being centrifuged twice at 10.000 RPM for 10 min at 4° C. using a Sorvall centrifuge (Newton, Conn., USA) equipped with a GSA600 rotor. The supernatant was stored at −20° C. until further use. Before inoculation, the cucumber juice was diluted in 1 volume of 0.2 M potassium-phosphate buffer (pH 5.8). The final pH was adjusted to 6.0 and the cucumber medium was forced through a 0.22 μm filter to assure sterility. When mentioned, both fruit media were supplemented with p-ABA till a final concentration of 10 mg/L.

2.1.3 Fermentation

The cucumber and CDM media were inoculation with *L. reuteri* control (pNZ7021; empty vector) and folate overproducer (pNZ7026; folate gene cluster overexpressing plasmid). Inoculated media were cultivated for 40 hours at 37° C.

2.1.4 Folate Measurements

Total folate content was measured using the microbiological assay described by Horne and Patterson (1988, Clin Chem 34:2357-2359) or by Sybesma et al. 2003 (Appl. Environm. Microbiol 69: 3069-3076). Folate samples were taken after approximately 40 hours of growth from culture from stationary phase.

2.2 Results

Folate production pools are shown in Tables 1 and 2 for *L. reuteri* JCM1112

TABLE 1

Fermentation of *L. reuteri* strain JCM1112 on 80% cucumber juice medium

| Strain | Total folate production pool μg/L | Standard deviation, μg/L | Total folate production pool μg/L per $OD_{600}$ | Fold* increase of folate pools compared to Table 2 |
|---|---|---|---|---|
| +pNZ7021[a] | 22.14 | 1.00 | 8.64 | 0.32× |
| +pNZ7026[b] | 64.00 | 7.00 | 33.77 | n.d. |
| +pNZ7026 + p-ABA[c] | 385.99 | 19.34 | 501.37 | 0.09× |
| Blanc[d] | 9.96 | 0.44 | | | n.d. = not determined
[a] empty vector
[b] folate overproduction plasmid
[c] folate overproduction plasmid, containing additional 10 mg/L p-ABA
[d] cucumber juice
*fold increase is calculated based on the total folate production pool.

TABLE 2

Fermentation of *L. reuteri* strain JCM1112 on CDM medium with p-ABA

| Strain | Total folate production pool μg/L | Standard deviation, μg/L | $OD_{600}$ |
|---|---|---|---|
| +pNZ7021[a] | 69.05 | 8 | 2.75 |
| +pNZ7026[b] | 4449.05 | 201 | 2.42 |

[a] empty vector
[b] folate overproduction plasmid 2.3 Conclusion

The results show that folate production of the recombinant *Lactobacillus reuteri* strains can not be enhance when cucumber juice is used as fermentation medium, when compared to CDM. These experiments clearly show that ability to produce high folate pools depends on the type of fruit juice that is used as broth.

Example 3

Fermentation Broth with Increased Folate:Vitamin B12 Ratios

The ratio of folate and B12 production was determined after fermentation of *L. reuteri* on CDM and melon juice. The experiments were performed as described above, however, additionally samples were taken for B12 analysis.

3.1 Materials and Methods 3.1.1 Strains and Inoculum Preparation

The following strains were used: *Lactobacillus reuteri* JCM1112 and *Lactobacillus plantarum* WCFS1. For both strains a 1% inoculum was used for inoculation of the developed media.

3.1.2 Fermentation

The melon and CDM media were inoculation with *L. reuteri* wild-type, control (pNZ7021; empty vector) and folate overproducer (pNZ7026; folate gene cluster overexpressing plasmid). Inoculated media were cultivated for 40 hours at 37° C.

3.1.3 B12 Measurements

Vitamin B12 content was determined according to the Official Methods of Analysis of AOAC International, using the *L. delbrueckii* subsp. *lactis* ATCC 7830 vitamin $B_{12}$ assay (Horowitz, W. (ed.). 2006. Official methods of analysis of AOAC International, 18th ed. AOAC International, Gaithersburg, Md.). Cell extracts of stationary phase cultures for $B_{12}$ analysis were prepared as previously described (Taranto, M. P., J. L. Vera, J. Hugenholtz, G. F. De Valdez, and F. Sesma. 2003. *Lactobacillus* reuteri CRL1098 produces cobalamin. J Bacteriol 185:5643-7.).

3.1.4 Folate Measurements

Total folate content was measured using the microbiological assay described by Horne and Patterson (1988, Clin Chem 34:2357-2359) or by Sybesma et al. 2003 (Appl. Environm. Microbiol 69: 3069-3076). Folate samples were taken after approximately 40 hours of growth from culture from stationary phase.

3.2 Results

Results are shown in FIGS. 1 and 2.

3.3 Conclusion

Figure 1:
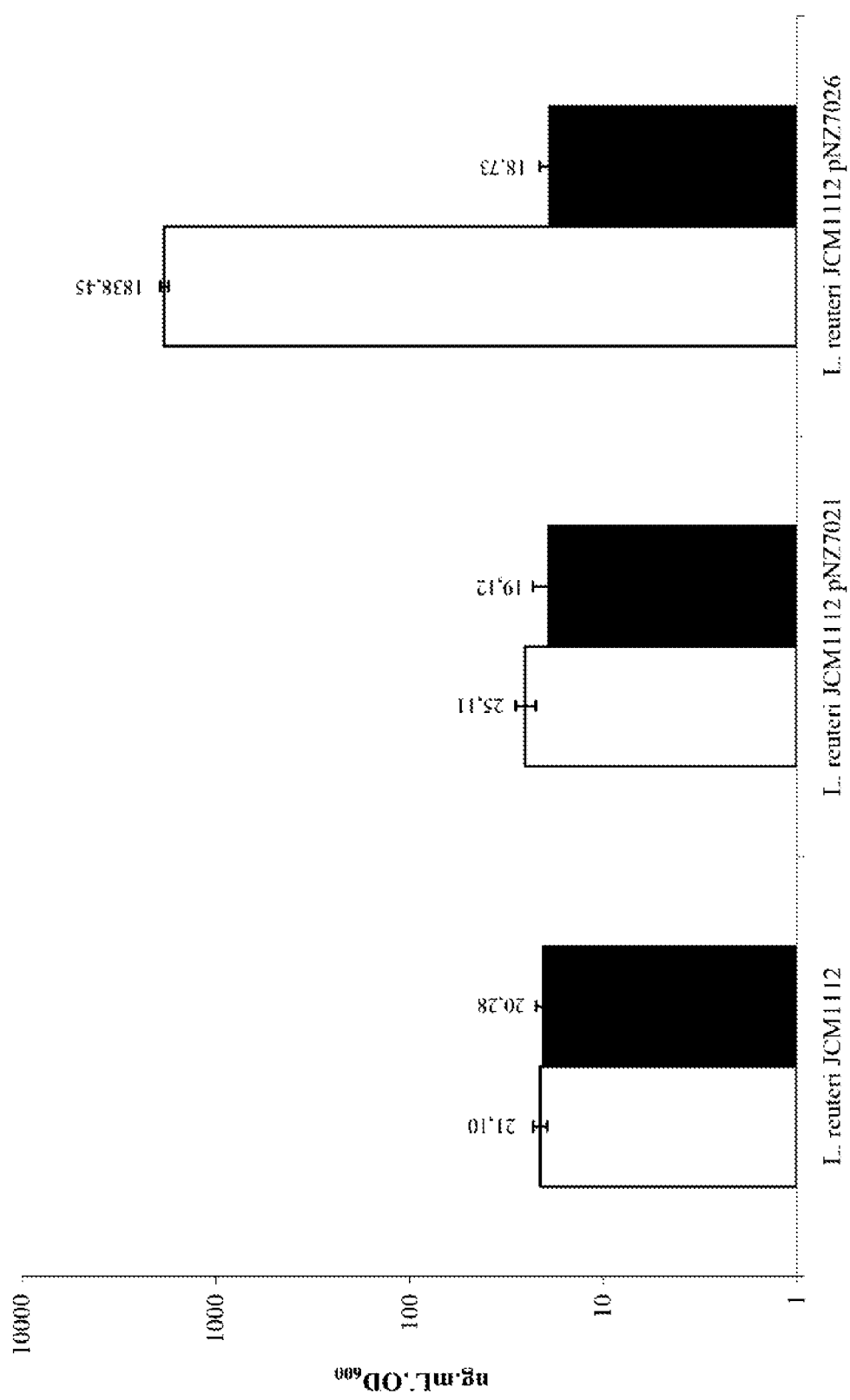
FIG. 1 shows folate production and B12 production pools after fermentation on CDM, for *L. reuteri* wild-type, control and folate overproducer. The white bars indicated folate pools, the black bars show B12 levels.
Figure 2:
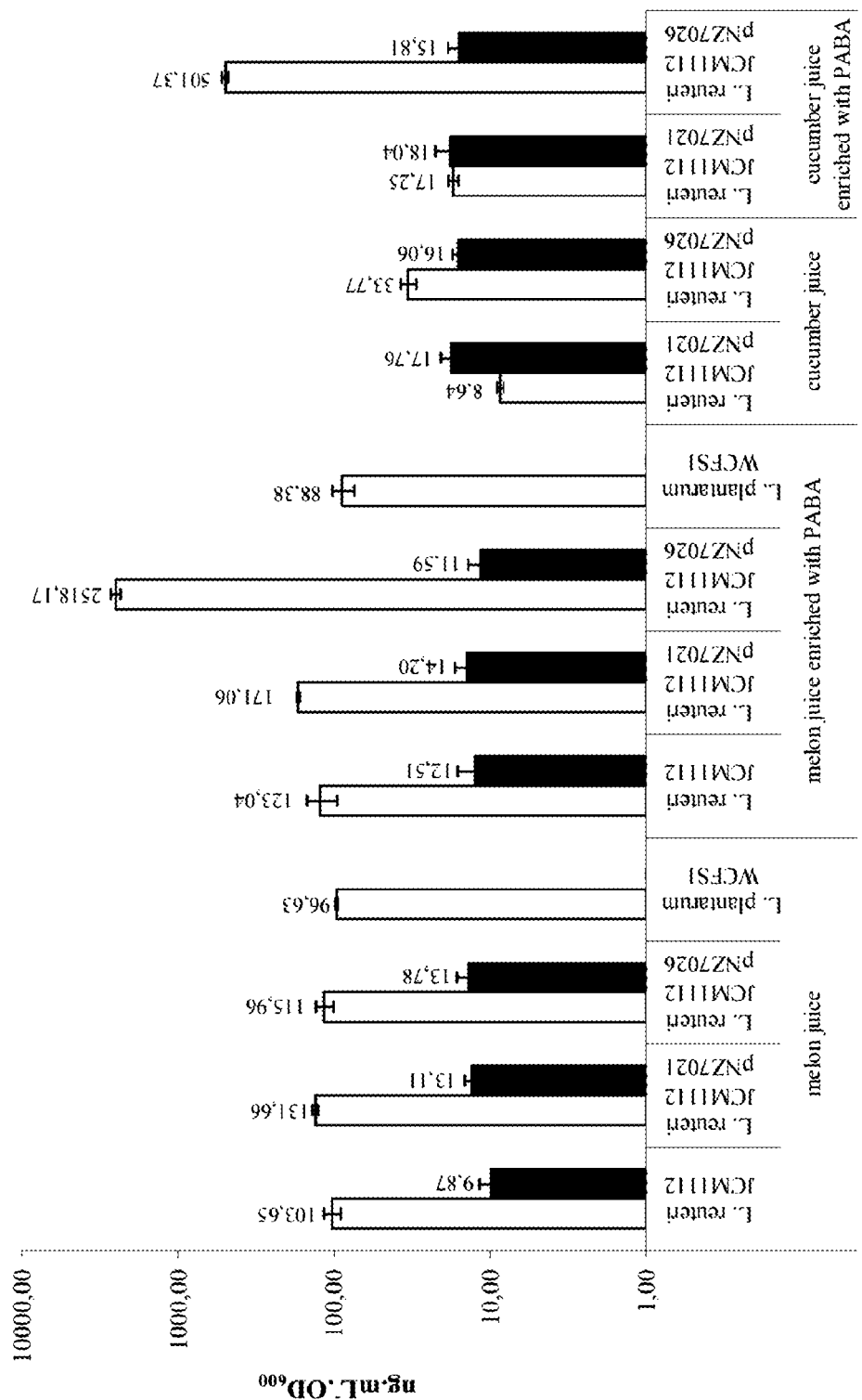
FIG. 2 shows folate production and B12 production pools after fermentation on cucumber and melon, for *L. plantarum*, *L. reuteri* wild-type, control and folate overproducer. The white bars indicated folate pools, the black bars show B12 levels.

The bacterium *L. reuteri* was able to produce folate and B12 ratio in a 1:1 ratio on CDM, for the wild-type and control strain. The overexpression of folate resulted in a folate to B12 ratio of 100 to 1. Melon juice fermentation is a nice way to increase the folate content, thereby, a more favourable folate to B12 ratio can be obtained. For the wild-type and control strain a 10:1 folate and B12 ratio was found, in the folate overproducing strain this was 250:1.

Example 4

Based on the three examples above a food product with beneficial properties is made. The food product is a fermented fruit juice that produces folate and B12 in suitable ratios. Moreover, *Lactobacilli* with probiotic properties to ferment melon juice and increase the folate content.

The invention claimed is:

1. A method for producing a medium fermented by *Lactobacillus* with increased total folate levels, comprising the following steps:
   (a) preparing a fermentation medium from all or a part of an extract of *Cucumis melo* melon fruit;
   (b) inoculating said fermentation medium with bacteria of one or more folate producing *Lactobacillus* strains; and
   (c) allowing fermentation to take place,
thereby producing said fermented medium with increased total folate levels.

2. The method according to claim 1, wherein said folate producing *Lactobacillus* strain is a wild type strain, mutant strain or recombinant strain.

3. The method according to claim 1, wherein said folate producing *lactobacillus* strain is a probiotic strain.

4. The method according to claim 1, wherein said folate producing *Lactobacillus* strain is a member of the species *L. reuteri* or *L. plantarum*.

5. The method according to claim 1 further comprising the step of adding para-aminobenzoic acid (p-ABA) to the fermentation medium during any of steps (a), (b), and (c).

6. The method according to claim 1 wherein said melon fruit extract is melon juice.

7. A method for preparing a food, feed or food supplement product, comprising producing a fermented medium with increased folate levels in accordance with claim 1, and using all or part of the medium to prepare said product.

8. A method for producing a medium fermented by *Lactobacillus* with increased total folate levels, comprising the following steps:
   (a) preparing a fermentation medium from all or a part of an extract of *Cucumis melo* melon fruit;

(b) inoculating said fermentation medium with bacteria of one or more folate producing *Lactobacillus* strains; and
(c) allowing fermentation to take place, thereby producing said fermented medium with increased total folate levels,
(d) killing or inactivating the bacteria in the medium and/or removing the bacteria from the medium.

9. The method according to claim 8, wherein the folate producing *Lactobacillus* strain is a member of the species *L. reuteri*.

10. The method according to claim 4, wherein said folate producing *Lactobacillus* strain is a member of the species *L. reuteri*.

* * * * *

UNITED STATES PATENT AND TRADEMARK OFFICE
CERTIFICATE OF CORRECTION

PATENT NO. : 8,524,297 B2  
APPLICATION NO. : 12/811782  
DATED : September 3, 2013  
INVENTOR(S) : Wegkamp et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 449 days.

Signed and Sealed this

Fifteenth Day of September, 2015

Michelle K. Lee
*Director of the United States Patent and Trademark Office*